(12) United States Patent
Hardy et al.

(10) Patent No.: US 9,610,167 B2
(45) Date of Patent: Apr. 4, 2017

(54) GLENOID EXTENSION BLOCK

(71) Applicant: Arthrex, Inc., Naples, FL (US)

(72) Inventors: Philippe Hardy, Paris (FR); Stéphane Naudin, Kailling (DE)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 14/965,582

(22) Filed: Dec. 10, 2015

(65) Prior Publication Data

US 2016/0095709 A1    Apr. 7, 2016

Related U.S. Application Data

(62) Division of application No. 13/777,782, filed on Feb. 26, 2013, now Pat. No. 9,216,091.

(30) Foreign Application Priority Data

Feb. 27, 2012 (EP) ..................................... 12157196

(51) Int. Cl.
*A61F 2/40* (2006.01)
*A61F 2/30* (2006.01)
*A61F 2/46* (2006.01)

(52) U.S. Cl.
CPC ........ *A61F 2/4081* (2013.01); *A61F 2/30767* (2013.01); *A61F 2/4612* (2013.01); *A61F 2002/30261* (2013.01)

(58) Field of Classification Search
CPC ........ A61F 2/4081; A61F 2/4059; A61F 2/40; A61F 2/42; A61F 2/4612; A61F 2/4609; A61F 2002/4085; A61F 2002/4088; A61F 2002/4092; A61F 2002/4096; A61F 2002/4059; A61F 2002/4062; A61F 2002/4066; A61F 2002/407; A61F 2002/4074; A61F 2002/4077; A61F 2002/4081; A61F 2002/4619–2002/4642
USPC ............................. 606/86 R, 87, 91, 96, 99
See application file for complete search history.

(56) References Cited

U.S. PATENT DOCUMENTS

| | | |
|---|---|---|
| 3,694,820 A | 10/1972 | Scales et al. |
| 4,502,161 A | 3/1985 | Wall |
| 5,108,440 A | 4/1992 | Grundei et al. |
| 6,761,740 B2 | 7/2004 | Tornier |
| 6,814,757 B2 | 11/2004 | Kopylov et al. |
| 7,124,762 B2 | 10/2006 | Carter et al. |
| 7,819,924 B2 | 10/2010 | VanDer Meulen et al. |
| 8,052,755 B2 | 11/2011 | Naidu |
| 8,110,006 B2 | 2/2012 | Reiley |
| 8,257,444 B2 | 9/2012 | Linares |
| 8,758,445 B2 | 6/2014 | Gupta et al. |
| 8,845,724 B2 | 9/2014 | Shenoy et al. |
| 8,845,744 B2 | 9/2014 | Winslow et al. |
| 9,216,091 B2 * | 12/2015 | Hardy .................. A61F 2/4081 |
| 9,232,955 B2 * | 1/2016 | Bonin, Jr. ............. A61B 17/15 |
| 9,283,076 B2 * | 3/2016 | Sikora ................ A61F 2/30756 |
| 2004/0148026 A1 | 7/2004 | Bonutti |

(Continued)

*Primary Examiner* — Alvin Stewart
(74) *Attorney, Agent, or Firm* — Blank Rome LLP

(57) ABSTRACT

A glenoid implant has an anatomically formed body including of metal and/or plastic materials. It further has a contact surface adapted to extend the surface of a glenoid and to bear a humerus. In the implant body, there is at least one hole with a screw head seating area for holding the head of a screw, which may be screwed into a glenoid for fixedly attaching the glenoid implant.

6 Claims, 3 Drawing Sheets

(56) References Cited

U.S. PATENT DOCUMENTS

| | | | |
|---|---|---|---|
| 2005/0049710 A1* | 3/2005 | O'Driscoll | A61F 2/3804 623/20.11 |
| 2005/0137709 A1 | 6/2005 | Klotz et al. | |
| 2005/0182493 A1* | 8/2005 | Bertram | A61B 17/1746 623/22.38 |
| 2006/0079963 A1 | 4/2006 | Hansen | |
| 2006/0116771 A1 | 6/2006 | Cooney et al. | |
| 2006/0241778 A1 | 10/2006 | Ogilvie | |
| 2007/0179624 A1 | 8/2007 | Stone et al. | |
| 2008/0058949 A1 | 3/2008 | Dees et al. | |
| 2009/0259314 A1 | 10/2009 | Linder-Ganz et al. | |
| 2009/0281632 A1 | 11/2009 | Naidu | |
| 2009/0287309 A1* | 11/2009 | Walch | A61L 27/047 623/18.11 |
| 2009/0318976 A1 | 12/2009 | Gabriel et al. | |
| 2009/0318977 A1 | 12/2009 | Di Giacomo et al. | |
| 2010/0023126 A1 | 1/2010 | Grotz | |
| 2010/0049327 A1* | 2/2010 | Isch | A61F 2/34 623/19.12 |
| 2010/0069974 A1* | 3/2010 | Oren | A61B 17/1714 606/86 R |
| 2010/0087928 A1 | 4/2010 | Graham et al. | |
| 2010/0131069 A1 | 5/2010 | Halbrecht | |
| 2011/0144760 A1 | 6/2011 | Wong et al. | |
| 2011/0213372 A1* | 9/2011 | Keefer | A61B 17/1659 606/85 |
| 2011/0264153 A1* | 10/2011 | Hassler | A61B 17/1684 606/86 R |
| 2011/0295375 A1* | 12/2011 | Appenzeller | A61B 17/1684 623/18.11 |
| 2012/0022655 A1 | 1/2012 | Clifford | |
| 2012/0078258 A1* | 3/2012 | Lo | A61B 17/15 606/87 |
| 2012/0109137 A1* | 5/2012 | Iannotti | A61B 17/1728 606/87 |
| 2012/0109226 A1* | 5/2012 | Iannotti | A61B 17/88 606/86 R |
| 2012/0123420 A1* | 5/2012 | Honiball | A61B 17/1764 606/87 |
| 2012/0239043 A1* | 9/2012 | Lappin | A61B 17/1631 606/80 |
| 2012/0296434 A1 | 11/2012 | Kumar | |
| 2013/0150977 A1 | 6/2013 | Gabriel et al. | |
| 2013/0261629 A1* | 10/2013 | Anthony | A61F 2/4014 606/80 |
| 2013/0261753 A1* | 10/2013 | Lappin | A61F 2/30734 623/19.11 |
| 2013/0331849 A1* | 12/2013 | Splieth | A61B 17/92 606/99 |
| 2014/0107715 A1* | 4/2014 | Heilman | A61B 17/1739 606/86 R |
| 2014/0142578 A1* | 5/2014 | Hananouchi | A61B 17/1746 606/87 |
| 2014/0163565 A1* | 6/2014 | Bollinger | A61B 17/1746 606/91 |
| 2014/0257304 A1* | 9/2014 | Eash | A61B 17/1739 606/87 |
| 2014/0316526 A1 | 10/2014 | Grotz | |
| 2015/0112348 A1* | 4/2015 | Schoenefeld | A61B 17/1746 606/87 |
| 2015/0157462 A1* | 6/2015 | Ek | A61F 2/4081 623/19.11 |
| 2015/0223941 A1* | 8/2015 | Lang | A61B 17/15 623/19.11 |
| 2016/0120555 A1* | 5/2016 | Bonin, Jr. | A61B 17/15 606/87 |
| 2016/0193051 A1* | 7/2016 | Budhabhatti | A61F 2/30734 623/19.11 |

\* cited by examiner

GLENOID EXTENSION BLOCK

CROSS-REFERENCE TO RELATED APPLICATIONS

This is a divisional of U.S. application Ser. No. 13/777,782, filed Feb. 26, 2013, which claims priority to pending European Application No. 12157196.2, filed on Feb. 27, 2012.

BACKGROUND OF THE INVENTION

1. Field of the Invention

The invention relates to an implant for increasing stability of the shoulder and specifically in the treatment of anterior shoulder instability.

2. Description of Relevant Art

Fractures of the anterior glenoid may be caused by anterior shoulder dislocation. Such fractures, also known as Bankart lesion lead to continuing shoulder instability. WO 2008/015670 A2 and EP 2 135 566 A1 disclose instruments and methods for repairing such a fracture by fixing a coracoid graft to the glenoid. Here harvesting, shaping, drilling and shuttling require a significant amount of time and specific skills of the surgeon. Cup shaped and ball shaped joint prosthesis are disclosed in EP 1 815 825 A1, EP 1 510 190 A1, FR 2825 263 A1, FR 2 843 293 A1 and FR 2 578 162 A1.

SUMMARY OF THE INVENTION

The embodiments are based on the object of simplifying the repair of a fractured/degenerated anterior glenoid and to offer the surgeon reliable tools for repairing such fractures/degenerations.

Solutions of the problem are described in the independent claims. The dependent claims relate to further improvements of the invention.

The glenoid implant is an anatomically shaped body. It is not a full joint. Instead, it is an extension to an existing joint, specifically the glenoid. Its size is only a part of the size of the glenoid. It may include metal and/or plastic materials. It may furthermore include a metal like titanium, stainless steel or a plastic material like PEEK. It may also include any combination of such materials. The glenoid implant provides means for attachment to a glenoid. Attachment may be done by screws or other fixation means. The glenoid implant has a contact surface adapted to extend the surface of the glenoid and to bear the Humerus head or at least part of it. The contact surface is roughly planar or with a slight curvature. It is neither ball shaped nor cup shaped, as a full joint prosthesis may be. Preferably, the glenoid implant has no direct contact to the articulated areas of the joint.

The main advantage of this implant over the prior art is that the time and effort needed for harvesting, shaping and drilling can be saved. Furthermore, it can be placed and fixed more easily. Failure of the autograft like breakage or resorption during and after fixation are not likely to occur as in the prior art. Compared to joint prosthesis known from prior art, it is not necessary to remove the whole cartilage surface.

Preferably, the body of the glenoid implant is roughly cuboidal shaped and the contact surface may be a recess in a top surface of the implant.

It is furthermore preferred, if the body of the glenoid implant has rounded edges.

In a further preferred embodiment, the glenoid implant has at least one hole for inserting a screw to attach the glenoid implant to the glenoid. The hole preferably has a screw head seating area and preferably allows the screw to be mounted in a predetermined range of angles. Most preferably there are two holes.

In a further embodiment, there is at least one means for holding the implant by a tool. This tool may be a handle. Preferably, the means for holding is a hole, which may have non-circular shape to prevent rotation.

Preferably, there is at least one recess between mounting surface and the contact surface. There may any number of such recesses.

Preferably, glenoid implants are available in different sizes adapted to bone sizes and sizes of glenoid defects.

Preferably, a kit of glenoid implants includes a choice of different sized implants.

A further aspect of the invention relates to a method of repairing a fractured and/or degenerated anterior glenoid. In a first step, fractured particles are removed from the glenoid or in the case of a degenerated glenoid, the bone to implant contact surface is refreshed. In the same time or in the following step a mounting surface is generated at the glenoid, preferably by using a shaver and/or osteotome. In the next step, an appropriate size of glenoid implant is selected. Then the selected glenoid implant is positioned at the glenoid, preferably by using an implant-holding tool. In the next step, the location of the holes to be drilled into the glenoid may be marked. Alternatively, the holes may be drilled directly by using the glenoid implant as drilling jig. Then the screws are screwed into the holes. As a further alternative, the screws may be inserted without drilling or preliminary fixed wires. Some steps like selecting the size of the implant may be exchanged in the order with other steps without affecting the result of the method.

BRIEF DESCRIPTION OF THE DRAWINGS

In the following, the invention will be described by way of example, without limitation of the general inventive concept, on examples of embodiment and with reference to the drawings.

Figure 1:
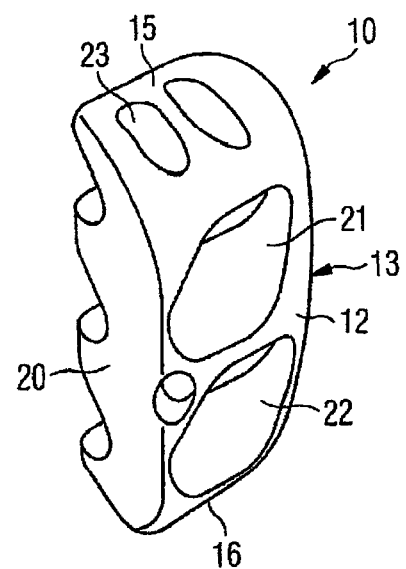
FIG. 1 shows the glenoid implant.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

In FIG. 1, a preferred embodiment is shown. The glenoid implant 10 has a mounting surface 11 by which it is attached to the glenoid. Mounting surface 11 may have a 3-dimensional structure contacting the glenoid to enhance bone ingrowth. The glenoid implant preferably has cuboidal shape. Although it may have any other shape as long as it allows fixation to the glenoid and adaption to the glenoid surface. There may be a rear surface 12 opposed to the mounting surface. The top surface 14 may have a recess serving as contact surface 20 adapted to the surface form of the glenoid 50 and to interface with the humerus head. Opposed to the top surface is a bottom surface 13. There are a first sidewall 15 and a second sidewall 16 which are preferably rounded. In the sidewall 15 there is a hole 23, which may be used to align the implant with at lest one guide pin, which has previously been placed in the bone. Furthermore, such a hole may be used by a handle for holding the implant. Two holes 21, 22 are protruding the glenoid implant from mounting surface to rear surface. They have an inner shape providing a screw head seating area for holding the head of a screw 40. They preferably allow orientation of the screw in a predetermined range of angles to provide flexibility in mounting.

Figure 2:
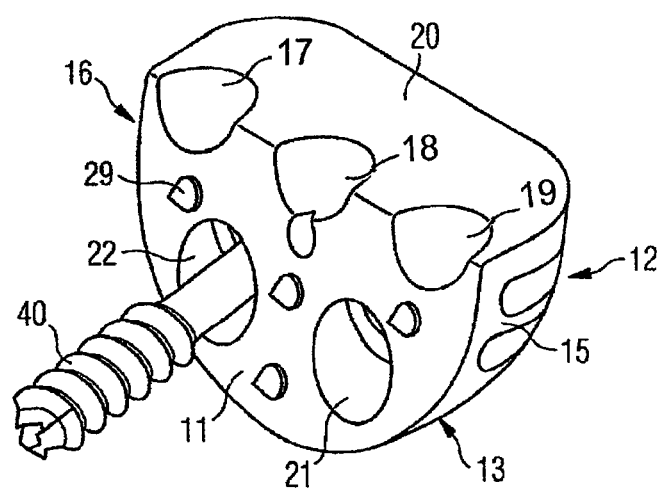
FIG. 2 shows a slightly modified design of the glenoid implant.

FIG. 2 shows a slightly modified design of the glenoid implant. Here the sidewalls 15, 16 are not rounded. Furthermore a screw 40 is inserted through hole 22. This screw is preferably a self-cutting screw. Between the mounting surface 11 and the contact surface 20 there are three recesses 17, 18, 19 through which suture anchors may be applied into the bone. There may any number of such recesses.

Figure 3:
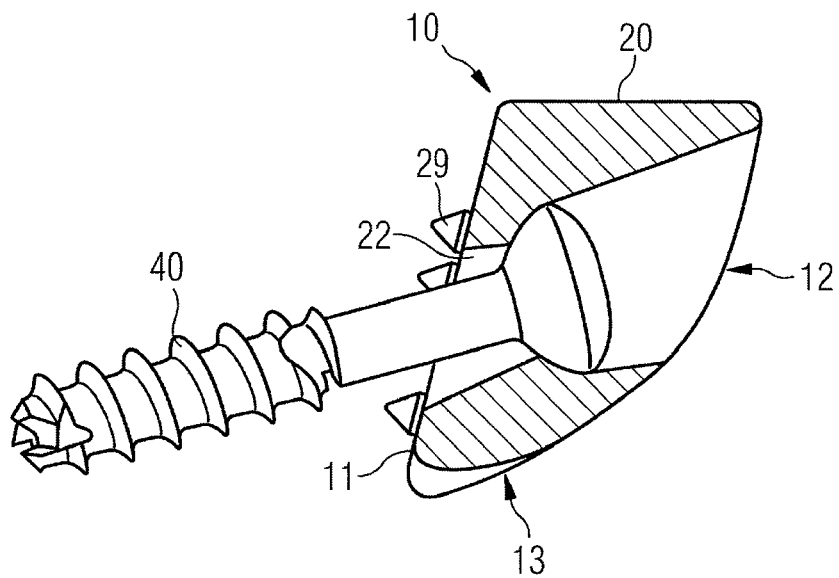
FIG. 3 shows a cutout view of the implant.

FIG. 3 shows a cutout view of the glenoid implant. This figure further shows a typical configuration of the holes 21, 22 for holding the screw 40. Furthermore, the protrusions 29 for improving fixation of the implant to the bone are shown in a side view. There is preferably at least one such protrusion and most preferably there is a plurality of such protrusions.

Figure 4:
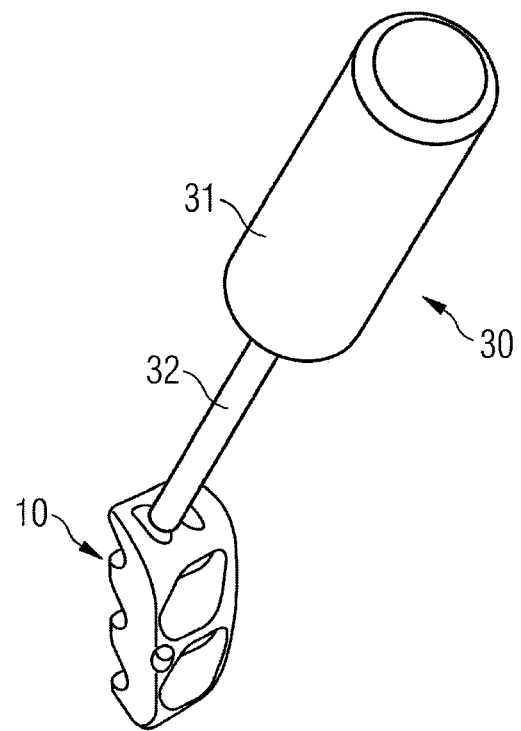
FIG. 4 shows the implant attached to a holding tool.

In FIG. 4, the implant 10 is shown attached to a holding tool 30. This holding tool includes a handle 31 attached to a shaft 32. The shaft has an end which fits into hole 23 of the implant. The surgeon may hold the implant at a selected location at the glenoid when drilling the screw holes and/or inserting the screws.

Figure 5:
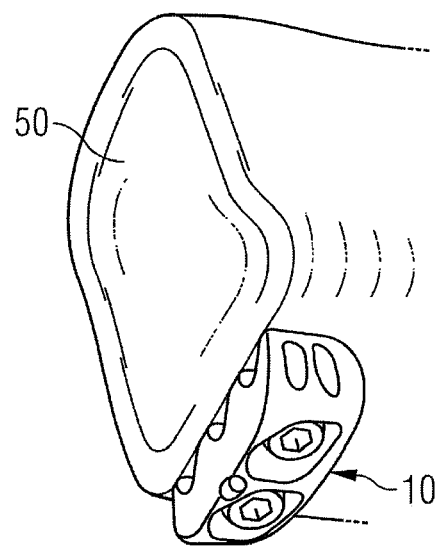
FIG. 5 shows the implant 10 attached to the glenoid 50.

FIG. 5 shows the implant 10 attached to a side of the glenoid 50. It only extends the glenoid and does not replace it.

Figure 6:
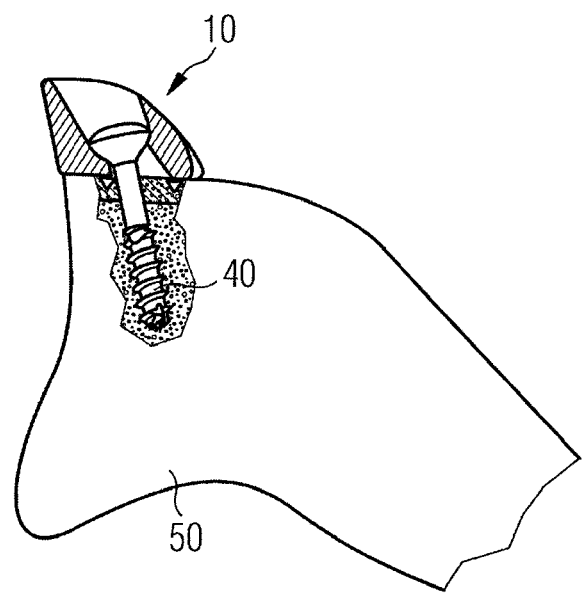
FIG. 6 shows a cross-section of an implant screwed to a glenoid.

In FIG. 6, a cross-section of the glenoid 50 is shown with a cross-section of the implant 10 attached thereto by means of the screw 40.

It will be appreciated to those skilled in the art having the benefit of this disclosure that this invention is believed to provide a joint implant. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of repairing a fractured or degenerated anterior glenoid by implanting a glenoid implant, comprising the steps of:
   (a) removing fractured particles from the glenoid or, in the case of a degenerated glenoid, refreshing the bone to implant contact surface;
   (b) generating a mounting surface at the glenoid without removing substantially the whole cartilage surface of the glenoid;
   (c) selecting the glenoid implant having an appropriate size;
   (d) positioning the selected glenoid implant at the glenoid without the implant having direct contact with articulated areas of the glenoid; and
   (e) advancing screws through the glenoid implant into the glenoid to secure the glenoid implant onto the glenoid.

2. The method of claim 1, wherein the step of generating a mounting surface at the glenoid is performed by using a shaver and/or osteotome.

3. The method of claim 1, wherein the step of positioning the selected glenoid implant at the glenoid is performed by using an implant-holding tool which fits into a holding means of the implant, the holding means being a hole having a substantially non-circular shape to prevent rotation.

4. The method of claim 1, comprising the additional step of predrilling holes in the glenoid for the screws securing the glenoid implant to the glenoid.

5. The method of claim 3, wherein the step of securing the selected glenoid implant with screws onto the glenoid is performed without drilling or preliminary fixed wires.

6. A method of repairing a fractured or degenerated anterior glenoid by implanting a glenoid implant, comprising the steps of:
   (a) removing fractured particles from the glenoid or, in the case of a degenerated glenoid, refreshing the bone to implant contact surface;
   (b) generating a mounting surface at the glenoid;
   (c) selecting the glenoid implant having an appropriate size;
   (d) positioning the selected glenoid implant at the glenoid by using an implant-holding tool which fits into a holding means of the implant, the holding means being a hole having a substantially non-circular shape to prevent rotation; and
   (e) advancing screws through the glenoid implant into the glenoid to secure the glenoid implant onto the glenoid.

* * * * *